(12) United States Patent
Mitchell

(10) Patent No.: US 6,436,065 B1
(45) Date of Patent: Aug. 20, 2002

(54) UPPER BODY SUPPORT

(75) Inventor: Timothy John Mitchell, Mount Barker (AU)

(73) Assignee: Bendezy PTY LTD, Albany (AU)

( * ) Notice: Subject to any disclaimer, the term of this patent is extended or adjusted under 35 U.S.C. 154(b) by 0 days.

(21) Appl. No.: 09/646,258
(22) PCT Filed: Mar. 11, 1999
(86) PCT No.: PCT/AU99/00147
§ 371 (c)(1),
(2), (4) Date: Nov. 1, 2000
(87) PCT Pub. No.: WO99/45863
PCT Pub. Date: Sep. 16, 1999

(30) Foreign Application Priority Data

Mar. 12, 1998 (AU) .............................................. PP2306

(51) Int. Cl.⁷ .................................................. A61F 5/00
(52) U.S. Cl. ............................... 602/19; 2/44; 482/124; 602/36
(58) Field of Search ........................... 602/19, 36; 2/44; 482/121, 122, 124; 606/241

(56) References Cited

U.S. PATENT DOCUMENTS

| | | | | | |
|---|---|---|---|---|---|
| 2,906,260 A | * | 9/1959 | Myers | .......................... | 602/19 |
| 5,860,944 A | * | 1/1999 | Hoffman | ........................ | 602/19 |
| 5,951,591 A | * | 9/1999 | Roberts | ......................... | 602/36 |
| 6,129,691 A | * | 10/2000 | Rupperts | ...................... | 602/19 |
| 6,190,342 B1 | * | 2/2001 | Taylor | ........................... | 602/19 |

* cited by examiner

Primary Examiner—Michael A. Brown
(74) Attorney, Agent, or Firm—Dougherty & Clements LLP

(57) ABSTRACT

In accordance with the present invention there is provided an upper body support characterized by a dorsal member, having a lower portion which extends substantially rearwardly of a wearer, and at least one flexibly resilient element operatively interconnected with the lower portion of the dorsal member so that when the wearer bends at the waist, the dorsal member operates on the or each flexible resilient element in such a manner that the weight of the upper body of the wearer is borne at least partly therethrough.

22 Claims, 5 Drawing Sheets

UPPER BODY SUPPORT

FIELD OF THE INVENTION

The present invention relates to an upper body support. More particularly, the upper body support of the present invention is intended for use in circumstances requiring bending at the waist.

BACKGROUND ART

Activities which involve either bending at the waist for long periods, or repetitive bending and straightening, such as various horticultural applications, impart considerable demands on the lower back and may cause injury thereto. One means of overcoming this problem utilised in existing devices is the creation of tension in a flexibly resilient element when a wearer of such devices bends at the waist. This tension provides support and is of assistance when the wearer wishes to regain an upright posture.

These prior art devices invariably rely heavily on a series of lengths of flexible material to maintain the flexibly resilient element in position. Further, during the use of such devices, the flexibly resilient element may shift from its most effective position, and may be uncomfortable to wear for extended periods. Further still, such flexible material is of limited utility in spreading a load across the back of the wearer.

The level of assistance offered by existing devices is inherently dependent on the properties of the material from which the flexibly resilient element is constructed. This construction limits the magnitude of the support able to be given to the wearer.

Other existing devices require a wearer to be attached to a fixed structure, and thus are of limited utility where the wearer must remain mobile, such as in many horticultural applications.

The upper body support of the present invention has as one object thereof to overcome substantially the above mentioned problems associated with the prior art.

Throughout the specification, unless the context requires otherwise, the word "comprise", or variations such as "comprises" or "comprising", will be understood to imply the inclusion of a stated integer or group of integers but not the exclusion of any other integer or group of integers.

DISCLOSURE OF THE INVENTION

In accordance with the present invention there is provided a upper body support comprising a dorsal member, a bracing assembly and at least one flexibly resilient element, the dorsal member having a lower portion which extends substantially rearwardly of a wearer, characterised in that the bracing assembly is adapted to be positioned in the lumbar region of the wearer and the or each flexibly resilient element operatively interconnected with the lower portion of the dorsal member so that when the wearer bends at the waist, the dorsal member operates on the or each flexibly resilient element through the bracing assembly in such a manner that the weight of the upper body of the wearer is borne at least partly by the or each flexibly resilient element.

Preferably, the upper body support is further provided with a shoulder bracing assembly, adapted to be positioned in or about the shoulder region of the wearer's back. Preferably still, the dorsal member is pivotally attached to each of the lumbar and shoulder bracing assemblies.

In a preferred form of the invention, the or each bracing assembly comprises a substantially rigid brace plate. Preferably still, the dorsal member is pivotally attached to the or each rigid brace plate.

Preferably, the or each flexibly resilient element is operatively interconnected with a lower terminus of the lower portion of the dorsal member.

In one form of the invention, the or each flexible resilient element is provided in the form of a spring.

Preferably, the upper body support of the present invention is further characterised in that two flexibly resilient elements are provided, each flexibly resilient element being adapted to act on a foot of the wearer, whereby the weight of the upper body of the wearer bent at the waist is substantially borne through the dorsal member and by the feet of the wearer.

Each bracing assembly preferably further comprises one or more lengths of flexible material adapted to facilitate the fastening of each plate to the body of the wearer.

In a highly preferred form of the invention, the brace plate of the lumbar bracing assembly is provided with two lengths of flexible material each provided with complimentary releasable fastening means of known type which may be releasably engaged to form an adjustable waist strap.

Further and still highly preferably, the brace plate of the shoulder bracing assembly is provided with two lengths of flexible material adapted to be fastened to the waist strap to form shoulder straps. Preferably each shoulder strap is provided with a means for adjustment of the length thereof.

Preferably still, each length of flexible material provided about the brace plate of the lumbar bracing assembly is further provided with a slidable anchoring point, with the lengths of flexible material provided about the brace plate of the shoulder bracing assembly being attached thereto.

The dorsal member is preferably of a cranked configuration, having upper, intermediate and lower portions. Still preferably, the dorsal member is pivotally attached to the shoulder bracing assembly on its upper portion, and to the lumbar bracing assembly at or about the junction of the intermediate and lower portions.

Preferably, the upper and lower portions of the dorsal member are of variable length. Preferably still, the upper and lower portions of the dorsal member each comprise an extendible element telescopingly received within a sleeve element. Further and still preferably, each of the upper and lower portions of the dorsal member is provided with a mechanism for adjustably fixing the extendible element in a particular position relative to the sleeve element.

In a preferred form of the invention, an anchor plate is releasably provided at or about a lower terminus of the extendible element of the lower portion of the dorsal member, the anchor plate being adapted to operatively interconnect the flexibly resilient elements to the lower terminus of the extendible element of the lower portion of the dorsal member at a point removed therefrom.

Preferably still, the anchor plate is adapted to be attached to the extendible element of the lower portion of the dorsal member in at least two different orientations.

In a highly preferred form of the invention, the anchor plate is adapted to be attached to the extendible element of the lower portion of the dorsal member in two different orientations, such that in a first orientation the anchor plate extends outward from the lower terminus of the extendible element of the lower portion of the dorsal member thereby effectively lengthening such, and in a second orientation the anchor plate extends inward from the lower terminus of the extendible element of the lower portion of the dorsal member thereby effectively shortening such.

In a highly preferred form of the invention, the extendible element of the upper portion of the dorsal member is pivotally attached to the brace plate of the shoulder bracing assembly.

Preferably, each flexibly resilient element is in communication with at least one of the feet of the wearer by way of a leg assembly comprising a segment of cable and a stirrup assembly adapted to receive a foot of the wearer. Preferably still, the length of the segment of cable is adjustable. Further and still preferably, slidably attached to the segment of cable is a means for the securing of the cable to a leg of the wearer, for example two lengths of flexible material provided with complimentary components of a hoop and loop type fastener.

In a highly preferred form of the invention, cushioning is provided on the brace plates and the shoulder straps.

BRIEF DESCRIPTION OF THE DRAWINGS

The upper body support of the present invention will now be described, by way of example only, with reference to one embodiment thereof and the accompanying drawings, in which: FIG.

BEST MODE(S) FOR CARRYING OUT THE INVENTION

Figure 1:
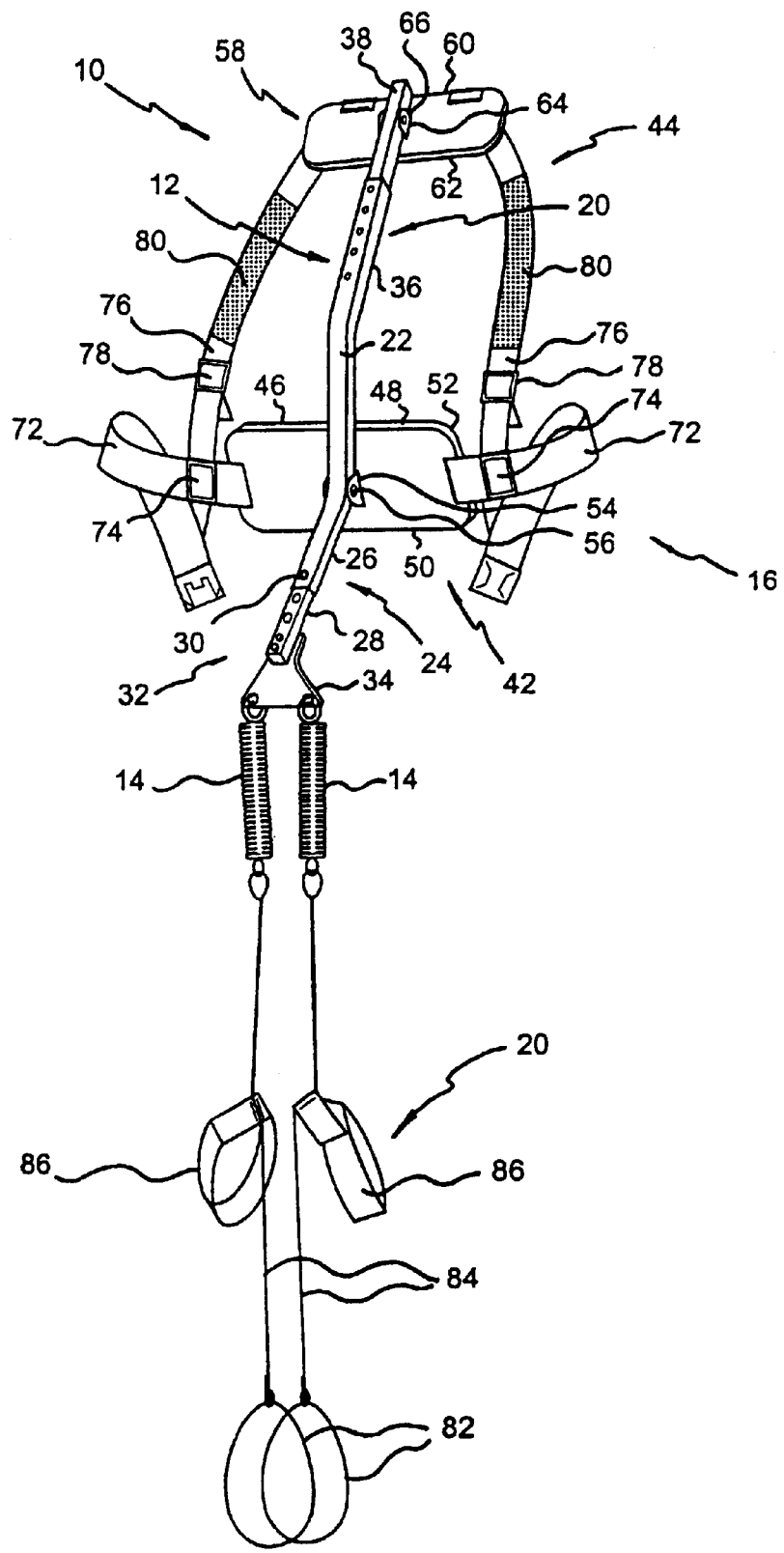
FIG. 1 is a rear perspective representation of the upper body support, in accordance with the present invention, showing in particular a dorsal member.
Figure 2:
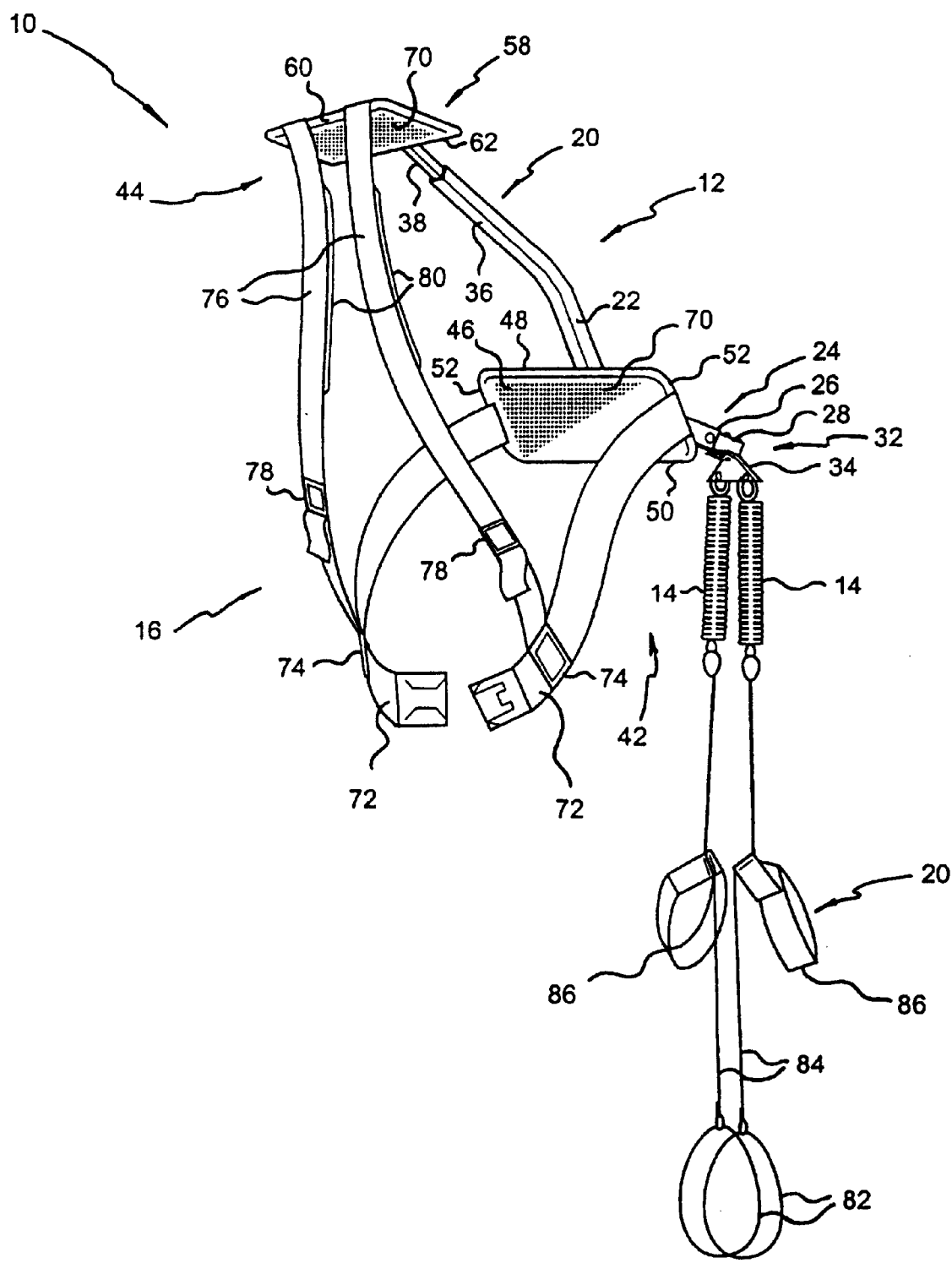
FIG. 2 is a front perspective representation of the upper body of FIG. 1.
Figure 3:
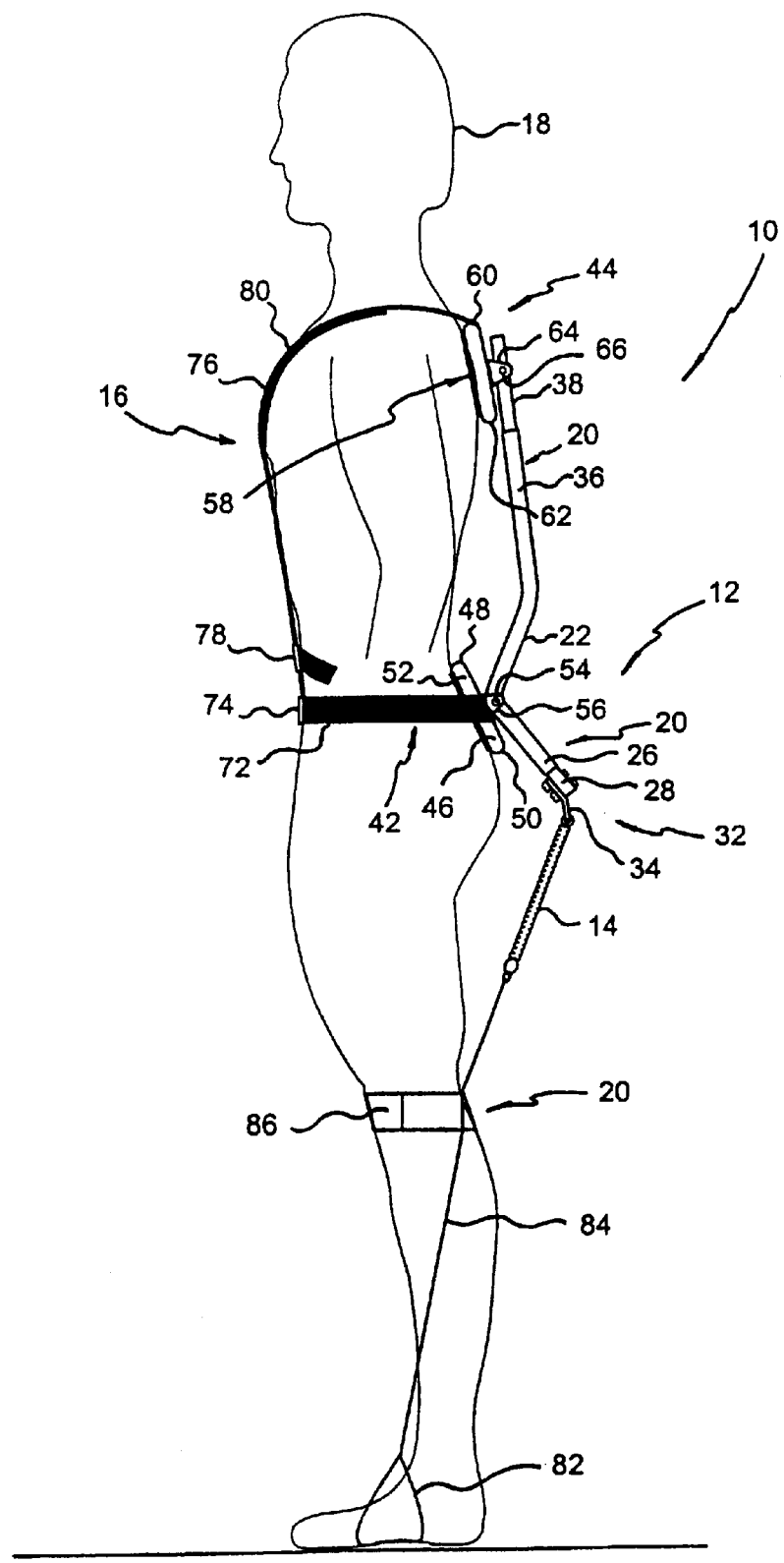
FIG. 3 is a side view of the upper body support of FIG. 1 being worn by a wearer in an upright stance, showing in particular the manner in which a lower length of a dorsal member extends substantially rearwardly of a wearer.
Figure 4:
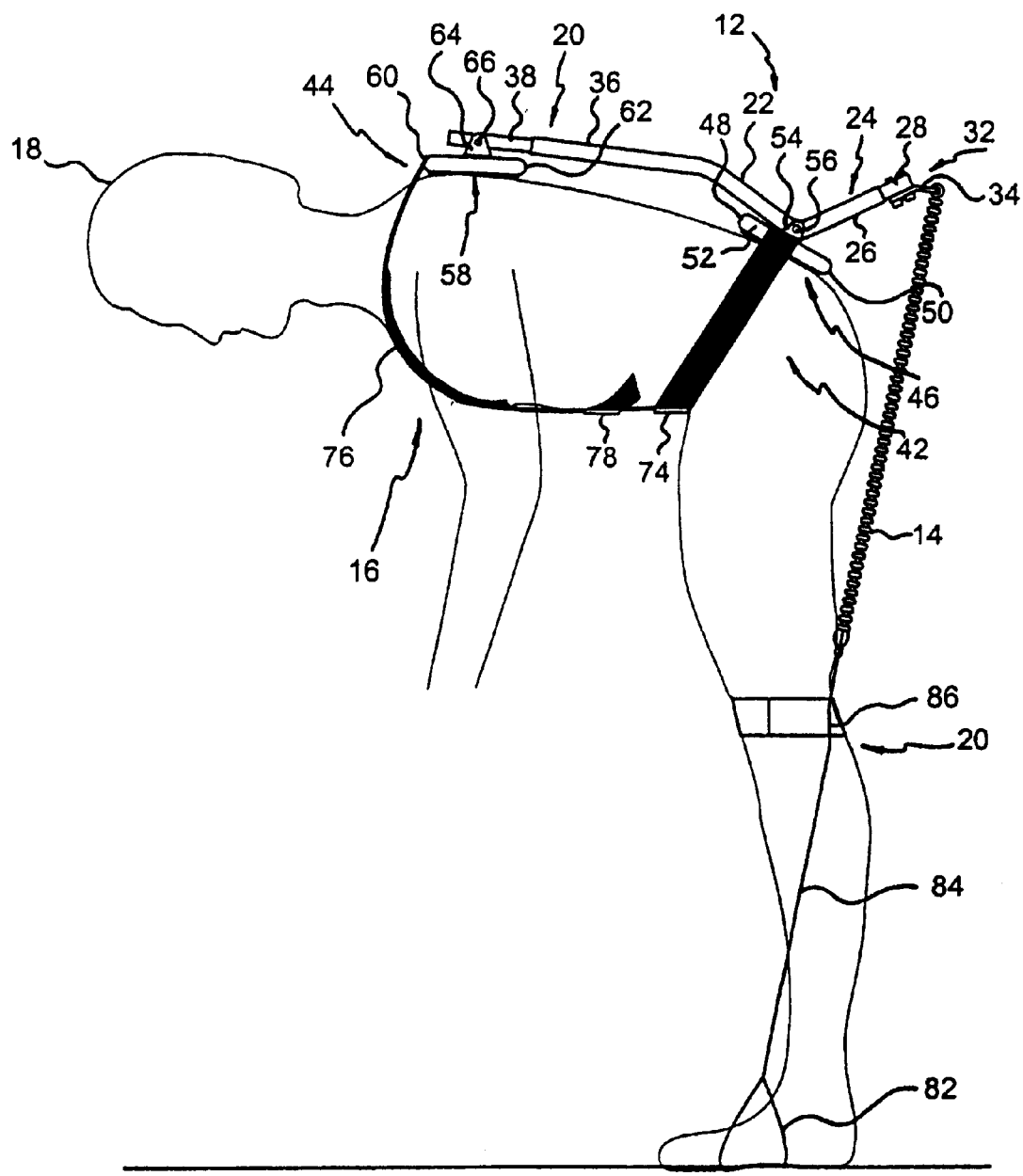
FIG. 4 is a side view of the upper body support and wearer of FIG. 2, the wearer having bent at the waist.
Figure 5:
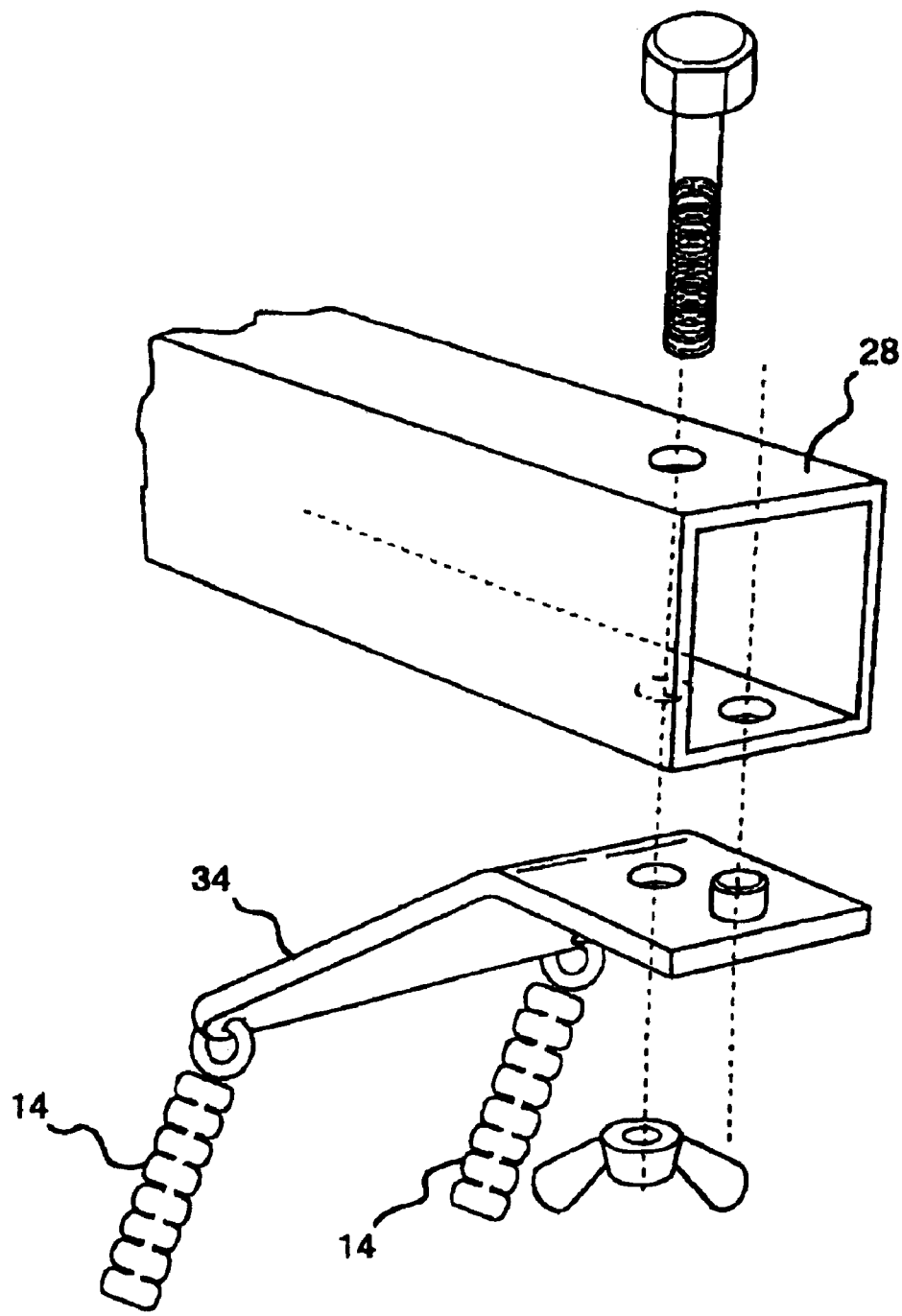
FIG. 5 is a perspective detail view of a lower terminus of the dorsal member of the upper body support of FIG. 1.

In FIGS. 1 to 5 there is shown an upper body support 10 in accordance with the present invention. The upper body support 10 comprises a dorsal member 12, two flexibly resilient elements in the form of springs 14 depending therefrom, a securing means 16, adapted to secure of the dorsal member 12 to the upper body of a wearer 18 and two leg assemblies 20, adapted to attach the springs 14 to the lower body of the wearer 18, as shown in FIGS. 1 and 2.

The dorsal member 12 is of a cranked configuration, comprising upper 20, intermediate 22, and lower 24 portions. The lower portion 24 extends substantially rearwardly of the wearer 18, as can best be seen in FIG. 3. The lower portion 24 in turn comprises a sleeve element 26, telescopingly received within which is an extendible element 28.

The lower portion 24 further comprises a means 30 for adjustably fixing the extendible element 28 in a particular position relative to the sleeve element 26. Releasably provided about a terminus 32 of the lower portion 24 of the dorsal member 12 is an anchor plate 34 for the attachment of the springs 14 thereto, as can best be seen in FIG. 5. The anchor plate 34 is adapted to be attached to the terminus 32 of the lower portion 24 of the dorsal member 12 in an alternate orientation, thereby effectively varying the length of the lower portion 24 of the dorsal member.

The upper portion 20 similarly comprises a sleeve element 36, telescopingly received within which is an extendible element 38, and a means 40 for adjustably fixing the extendible element 38 in a particular position relative to the sleeve element 36.

The securing means 16 comprises a lumbar bracing assembly and a shoulder bracing assembly 42 and 44 respectively. The lumbar bracing assembly 42 further comprises an elongate, approximately rectangular, lumbar brace plate 46, having upper and lower edges 48 and 50, two outer edges 52 and two opposed flanges 54.

An aperture is provided through each of the opposed flanges 54, capable of receiving a releasable fastening means, such as a nut and bolt assembly 56. Similarly, an aperture is provided through the dorsal member 12 at or about the junction of the intermediate 22 and lower 24 portions thereof. The dorsal member 12 is pivotally attached about the centre of the lumbar brace plate 46 in a transverse orientation, by way of the nut and bolt assembly 56 being simultaneously received through the apertures in the opposed flanges 54 and the aperture at or about the junction of the intermediate 22 and lower 24 portions of the dorsal member 12.

The shoulder bracing assembly 44 comprises an elongate, approximately rectangular, shoulder brace plate 58, having upper and lower edges 60 and 62, and two opposed flanges 64. An aperture is provided through each of the opposed flanges 64, capable of receiving a releasable fastening means, such as a nut and bolt assembly 66. Similarly, an aperture is provided through the dorsal member 12 at or about a terminus 68 of the upper portion 20 thereof. The dorsal member 12 is pivotally attached about the centre of the shoulder brace plate 58 in a transverse orientation, by way of the nut and bolt assembly 66 being simultaneously received through the apertures in the opposed flanges 64 and the aperture at or about at or about the terminus 68 of the dorsal member 12.

Each of the brace plates 46 and 58 are provided with cushioning material 70 to facilitate the comfortable use of the upper body support apparatus 10 by the wearer 18.

Extending from both outer edges 52 of the lumbar brace plate 46 are lengths of flexible material each equipped with complimentary releasable fastening means in the form of waist straps 72, of such a length that they are capable of being releasably and adjustably secured around the waist of the wearer 18. Each waist strap 72 is additionally provided with an anchoring point 74 such that the position of each anchoring point 74 is adjustable along the length thereof.

Extending from the upper edge 60 of the shoulder brace plate 58 are further lengths of flexible material equipped with releasable fastening means, for example, shoulder straps 76, of such a length that they are capable of being secured over the shoulders of the wearer 18, and engaging with the waist straps 72 by way of the anchoring points 74 to securely attach the upper body support 10 to the upper body of the wearer 18. The shoulder straps 76 are further provided with means to facilitate the adjustment of the length thereof 78, and cushioning 80.

Each of the leg assemblies 20 of the body support 10 in turn comprise a stirrup arrangement 82, and a segment of cable 84 arranged such adjustment of the size of the stirrup 82 effects adjustment of the length of the cable 84. Each leg assembly 20 further comprises a means for releasably securing such to a leg of the wearer 18, for example a leg strap 86. The position of each leg strap 86 may be adjusted by sliding such along the segment of cable 84.

In use, the wearer 18 secures the upper body support 10 to their upper body by placing their arms through the shoulder straps 76. By sliding the extendible element 38 of the upper portion 20 relative to the sleeve element 36 and fixing such in position by way of the means 40, the upper edge 48 lumbar brace plate 46 is positioned in line with or below the top of the wearer's pelvis. The waist straps 72 may then be secured about the wearer's waist region, and adjusted to fit. The point of attachment of the shoulder straps 76 to the waist straps 72 may be varied for comfort by sliding the anchoring point 74 along the waist strap 74.

The wearer 18 then places their feet through the stirrup arrangement 82, adjusting the configuration thereof as necessary, and secures the leg straps 86 in a comfortable position about their lower leg. Typically, if the wearer 18 intends to engage in activities involving walking and bending, the straps 86 are fitted above the knee. If the wearer 18 intends to engage in activities involving squatting and bending, the straps 86 are typically fitted about the ankle.

When the wearer 18, bends at the waist, the lower portion 24 of the central dorsal member 12, which extends substantially rearwardly of the wearer, causes the dorsal member 12 to act on the springs 14, creating a tension therein, said tension supporting the upper body weight of the wearer 18 during activities requiring a bent posture over long periods, and additionally facilitating the user 18 in regaining an erect posture. The tension created in the springs 14 is transferred, through the construction of the leg assemblies 20, to the stirrup arrangements 82 and the feet of the wearer 18. The level of tension generated in the springs 14, and thus the level of support provided thereby, may be adjusted by sliding the extendible element 28 of the lower portion 24 relative to the sleeve element 26 and fixing such in position by way of the means 30. Lengthening the lower portion 24 of the dorsal member 12 generates greater tension in the springs 14, and is thus more suitable for heavier or taller wearers 18.

The level of tension generated in the springs 14, and thus the level of support provided thereby, may also be adjusted by altering the orientation of the anchor plate 34. It is envisaged that, having adjusted the extendible element 28 of the lower portion 24 to suit their height and weight, a wearer 18 might reverse the orientation of the anchor plate 34 to conveniently increase or decrease the level of support provided to suit a particular activity.

It is envisaged that the dorsal member 12, the lumbar bracing plate 46 and the shoulder bracing plate 58 would be manufactured from a light yet rigid material, such as aluminium or a suitable plastic.

It is further envisaged that the waist, shoulder and calf straps 72, 76 and 86 would be made of a flexible yet robust material such as poly webbing or canvas or a vinyl based material such as VYTVRA®, and that the releasable fastening means provided thereon may be of a hook and loop type, such as VELCRO®.

It is still further envisaged that segment of cable 84 may be provided in the form of a length of marine rope.

Modifications and variations such as would be apparent to the skilled addressee are considered to fall within the scope of the present invention.

The claims defining the invention are as follows:

1. An upper body support comprising a dorsal member, a bracing assembly and at least one flexibly resilient element, the dorsal member having a lower portion which extends substantially rearwardly of a wearer, characterized in that the bracing assembly is adapted to be positioned in the lumbar region of the wearer, and each flexibly resilient element being operatively interconnected with the lower portion of the dorsal member so that when the wearer bends at the waist, the dorsal member operates on each flexibly resilient element through the bracing assembly in such a manner that the weight of the upper body of the wearer is borne at least partly by each flexibly resilient element;

the upper body support being further provided with a shoulder bracing assembly adapted to be positioned in or about the shoulder region of the wearer's back;

the dorsal member being pivotally attached to each of the lumbar and shoulder bracing assemblies.

2. An upper body support in accordance with claim 1 characterized in that each flexibly resilient element is operatively interconnected with a lower terminus of the lower portion of the dorsal member.

3. An upper body support in accordance with any one of the preceding claims, characterised in that the or each flexible resilient element is provided in the form of a spring.

4. An upper body support in accordance with claim 1, characterised in that the dorsal member is pivotally attached to the shoulder bracing assembly on its upper portion, and to the lumbar bracing assembly at or about the junction of the intermediate and lower portions.

5. An upper body support comprising a dorsal member, a bracing assembly and at least one flexibly resilient element, the dorsal member having a lower portion which extends substantially rearwardly of a wearer, characterized in that the bracing assembly is adapted to be positioned in the lumbar region of the wearer, and each flexibly resilient element being operatively interconnected with the lower portion of the dorsal member so that when the wearer bends at the waist, the dorsal member operates on each flexibly resilient element through the bracing assembly in such a manner that the weight of the upper body of the wearer is borne at least partly by each flexibly resilient element;

wherein said bracing assembly comprises a substantially rigid brace plate.

6. An upper body support in accordance with claim 5, characterised in that the dorsal member is pivotally attached to the or each rigid brace plate.

7. An upper body support in accordance with any of claims 5 to 6, characterised in that each bracing assembly further comprises one or more lengths of flexible material adapted to facilitate the fastening of the or each brace plate to the body of the wearer.

8. An upper body support in accordance with claim 7, characterised in that two lengths of flexible material are provided about the brace plate of the lumbar bracing assembly, each length of flexible material being provided with complimentary releasable fastening means of known type which may be releasably engaged to form an adjustable waist strap.

9. An upper body support in accordance with claim 8, characterised in that two lengths of flexible material are provided about the brace plate of the shoulder bracing assembly, each length of flexible material being adapted to be fastened to the waist strap to form adjustable shoulder straps.

10. An upper body support in accordance with claim 8 or 9, characterised in that each length of flexible material provided about the brace plate of the lumbar bracing assembly is further provided with a slidable anchoring point, with the lengths of flexible material provided about the brace plate of the shoulder bracing assembly being attached thereto.

11. An upper body support in accordance with any one of the preceding claims, characterised in that the dorsal member is of a cranked configuration, having upper, intermediate and lower portions.

12. An upper body support in accordance with claim 4 or 11, characterised in that the upper and lower portions of the dorsal member are of variable length.

13. An upper body support in accordance with claim 12, characterised in that the upper and lower portions of the dorsal member each comprise an extendible element telescopingly received within a sleeve element.

14. An upper body support in accordance with claim 13, characterised in that each of the upper and lower portions of the dorsal member is provided with a mechanism for adjustably fixing the extendible element in a particular position relative to the sleeve element.

15. An upper body support in accordance with claim 14, characterised in that an anchor plate is releasably provided at or about a lower terminus of the extendible element of the lower portion of the dorsal member, the anchor plate being adapted to operatively interconnect the flexibly resilient elements to the lower terminus of the extendible element of the lower portion of the dorsal member at a point removed therefrom.

16. An upper body support in accordance with claim 15, characterised in that the anchor plate is adapted to be attached to the extendible element of the lower portion of the dorsal member in at least two different orientations.

17. An upper body support in accordance with claim 15 or 16, characterised in that the anchor plate is adapted to be attached to the extendible element of the lower portion of the dorsal member in two different orientations, such that in a first orientation the anchor plate extends outward from the lower terminus of the extendible element of the lower portion of the dorsal member thereby effectively lengthening such, and in a second orientation the anchor plate extends inward from the lower terminus of the extendible element of the lower portion of the dorsal member thereby effectively shortening such.

18. An upper body support in accordance with any one of claims 13 to 17, characterised in that the extendible element of the upper portion of the dorsal member is pivotally attached to the brace plate of the shoulder bracing assembly.

19. An upper body support comprising a dorsal member, a bracing assembly and at least one flexibly resilient element, the dorsal member having a lower portion which extends substantially rearwardly of a wearer, characterized in that the bracing assembly is adapted to be positioned in the lumbar region of the wearer, and each flexibly resilient element being operatively interconnected with the lower portion of the dorsal member so that when the wearer bends at the waist, the dorsal member operates on each flexibly resilient element through the bracing assembly in such a manner that the weight of the upper body of the wearer is borne at least partly by each flexibly resilient element;

characterised in that two flexibly resilient elements are provided, each flexibly resilient element being adapted to act on a foot of the wearer, whereby the weight of the upper body of the wearer bent at the waist is substantially borne through the dorsal member and by the feet of the wearer.

20. An upper body support comprising a dorsal member, a bracing assembly and at least one flexibly resilient element, the dorsal member having a lower portion which extends substantially rearwardly of a wearer, characterized in that the bracing assembly is adapted to be positioned in the lumbar region of the wearer, and each flexibly resilient element being operatively interconnected with the lower portion of the dorsal member so that when the wearer bends at the waist, the dorsal member operates on each flexibly resilient element through the bracing assembly in such a manner that the weight of the upper body of the wearer is borne at least partly by each flexibly resilient element;

wherein each flexibly resilient element is in communication with at least one of the feet of the wearer by way of a leg assembly comprising a segment of cable and a stirrup assembly adapted to receive a foot of the wearer.

21. An upper body support in accordance with claim 20, characterised in that the length of the segment of cable is adjustable.

22. An upper body support in accordance with claim 20 or 21, characterised in that a means for the securing of the cable to a leg of the wearer is slidably attached to the segment of cable.

* * * * *